US00PP08768P

United States Patent [19]

Hirabayashi et al.

[11] Patent Number: Plant 8,768

[45] Date of Patent: Jun. 7, 1994

[54] PETUNIA PLANT NAMED REVOLUTION WHITE

[75] Inventors: Hiroshi Hirabayashi, Yachiyo; Ushio Sakazaki, Ibaraki, both of Japan

[73] Assignees: Keisei Rose Nurseries, Inc., Tokyo; Suntory Limited, Osaka, both of Japan

[21] Appl. No.: 976,458

[22] Filed: Nov. 13, 1992

[51] Int. Cl.[5] ..... A01H 5/00

[52] U.S. Cl. ..... Plt./68.1

[58] Field of Search ..... Plt. 68.1

[56] References Cited

U.S. PATENT DOCUMENTS

P.P. 6,899 7/1989 Tsuda et al. .

P.P. 6,915 7/1989 Tsuda et al. .

*Primary Examiner*—James R. Feyrer
*Assistant Examiner*—E. F. McElwain
*Attorney, Agent, or Firm*—Burns, Doane, Swecker & Mathis

[57] ABSTRACT

Disclosed herein is a decumbent type petunia plant having long stems. The plant has abundant branching and a great profusion of blooms, and the whole bush remains in bloom for a considerable period of time. The flowers are single and large and the petals are a yellowish white color with vivid yellow green lines radiating from pale greenish yellow color bottom throat portion. The plant is highly resistant to rain, heat, and drought.

4 Drawing Sheets

BACKGROUND OF THE VARIETY

The present invention relates to a new and distinct variety of petunia plant obtained from bud mutation of 'Revolution Brilliantpink'.

Petunia is a very popular plant and is used for flower bedding and potting in the summer season. There are only a few varieties of the petunia plant which do not have an upright growth habit and which have a high resistance to rain, heat, drought and cold. Accordingly, this invention was aimed at obtaining a new variety of decumbent habit petunia plant having long stems, a great profusion of blooms, petal color is white, the bush remaining in bloom for a considerable period of time, and a high resistance to rain, heat, drought and cold.

The new variety of petunia plant according to this invention obtained accidentally from bud mutation of a crossed variety, 'Revolution Brilliantpink' (see, U.S. Plant Pat. No. 6,914), which originated from a crossing of 'Recoverer Scarletred' as the female parent and a wild type of petunia plant native to Brazil as the pollen parent, in 1989 at the Yachiyo Farm of Keisei Rose Nurseries, Inc., residing at 755 Ōwadasinden, Yachiyo-shi, Chiba-ken, Japan. The new variety of the present invention originated as a spontaneous bud mutation of unknown causation. The resulting new variety was propagated by cutting, and then grown as a trial by flower bedding. The botanical characteristics of the plants were then examined, using 'Revolution Brilliantpink' for comparison, from the spring of 1990. As a result, it was concluded that this petunia plant is clearly distinguishable from the comparative variety 'Revolution Briliantpink', in flower color, while maintaining beneficial characteristics thereof, and it is further distinguishable from any other variety, whose existence is known to us. This new variety of petunia plant has been named 'Revolution White'.

In the following description, the color-coding is in accordance with the Horticultural Colour Chart of the Royal Horticultural Society, London, England (RHS Color Chart), and the Japan Color Standard for Horticultural Plant (JHS Color Chart).

The variety, 'Revolution Brilliantpink', which induced bud mutation of this new variety, is presently maintained at the aforementioned Yachiyo Farm of the Keisei Rose Nurseries, Inc., and Plant Biotechnology Laboratory, Institute for Fundamental Research of Suntory Ltd., and is marketed worldwide. The main botanical characteristics of 'Revolution Brilliantpink' are as follows.

Plant:

*Growth habit.*—Decumbent. The stems hang down where potted in a hanging pot.

*Plant height.*—15–20 cm.

*Spreading area of plant.*—The stem extends to a length of 50–80 cm from the base, and thus the spreading area of the plant is 100–150 cm in diameter.

*Growth.*—Very vigorous with abundant branching, a great profusion of blooms; the whole bush remaining in bloom for a considerable period of time.

*Blooming period.*—Late March to late September, in the southern Kantō area, Japan. The plant shape does not change throughout this period.

Stem:

*Thickness.*—Main stem 2.5–3.5 mm; lateral stem 1.5–2.0 mm.

*Color.*—Strong yellow green (R.H.S. 144A - 145A, JHS 3507 - 3712).

*Pubescence.*—Normal.

*Branching.*—Over-abundant.

*Length of internode.*—1.5–1.7 cm before blooming; 3.0–4.0 cm during blooming.

Leaf:

*Phyllotaxis.*—Verticillate before blooming; opposite during blooming.

*Shape.*—Lanceolate.

*Size (average).*—6.0–7.0 cm×2.5–3.5 cm.

*Thickness.*—0.6–0.8 mm.

*Color.*—Moderate olive green to strong yellow green R.H.S. 146A - 143A, JHS 3508 - 3308).

*Pubescence.*—Few.

Flower: Opening obliquely upward.

*Type.*—Single.

*Shape.*—Funnel-shape, with five-fissured limb.

*Diameter.*—7.0–8.0 cm, large.

*Color.*—In the unopened stage (bud), dark reddish purple (R.H.S. 79A - 79B, JHS 9516 - 9210); when open, dark purplish red (R.H.S. 71A, JHS 9509); at full bloom, vivid purplish red (R.H.S. 74A, JHS 9507 - 9207), with deep reddish purple (R.H.S. 77A, JHS 9209 - 9210) lines radiating from a dark purple (R.H.S. 83A, JHS 8609 - 8610) center portion. The reverse side of the petal is a vivid reddish purple color (R.H.S. 74A, JHS 9208 - 9206). The petal has a metallic luster.

*Reproductive organs.*—1 normal pistil having a grayish olive green (R.H.S. 137A, JHS 3716) stigma, and 5 normal stamens each having a deep purple (R.H.S. 86A, JHS 8307) anther and a light purple (R.H.S. 87D, JHS 8603) filament.

*Peduncle.*—1.5–2.0 cm in thickness, and 1.5–2.0 cm in length.

Physiological and ecological characteristics: High resistance to rain, heat, and drought. Also high resistance to disease, particularly gray mold (Botrytis). Moderate resistance to pest.

This new and distinct variety of petunia plant, 'Revolution White', was asexually reproduced by cutting at the aforementioned Yachio Farm of Keisei Rose Nurseries, Inc., and Plant Biotechnology Laboratory, Institute for Fundamental Research of Suntory Ltd., and the homogeneity and stability thereof were confirmed.

SUMMARY OF THE VARIETY

The new variety of petunia plant has a decumbent habit and long stems, and thus is very different from a similar variety, 'Recoverer Scarletred', having an upright growth habit, and then is distinguishable from the indicated parent variety, 'Revolution Brilliantpink', having flower of vivid purplish red color with metallic luster. The plant has abundant branching and a great profusion of blooms, and the whole bush remains in bloom for a considerable period of time, longer than the blooming period of 'Recoverer Blue', and the same as that of 'Revolution Brilliantpink'. The flowers are single, and large, and petals are a yellowish white color (R.H.S. 155D, JHS 2501), with vivid yellow green lines radiating from a light purple center portion. The plant is highly resistant to rain, heat, and drought.

This variety, 'Revolution White', is substantially the same as the indicated parent variety, 'Revolution Brilliantpink', except for the color of flower.

DESCRIPTION OF THE VARIETY

Figure 1:
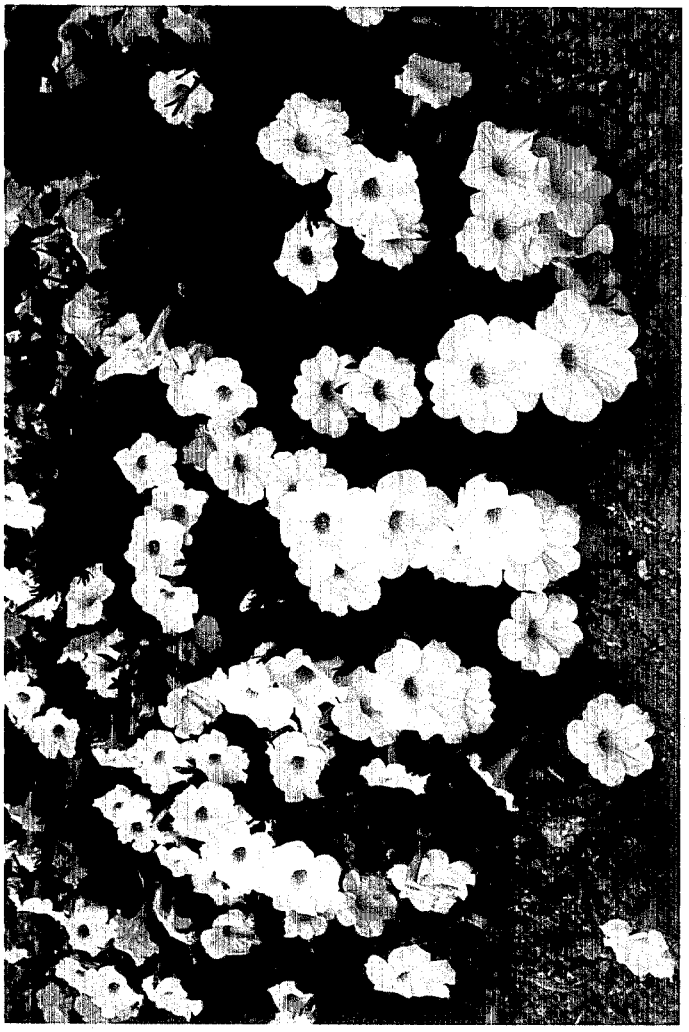
FIG. 1 is a photograph giving a partial view of the new variety of petunia plant planted in a flower bed.
Figure 2:
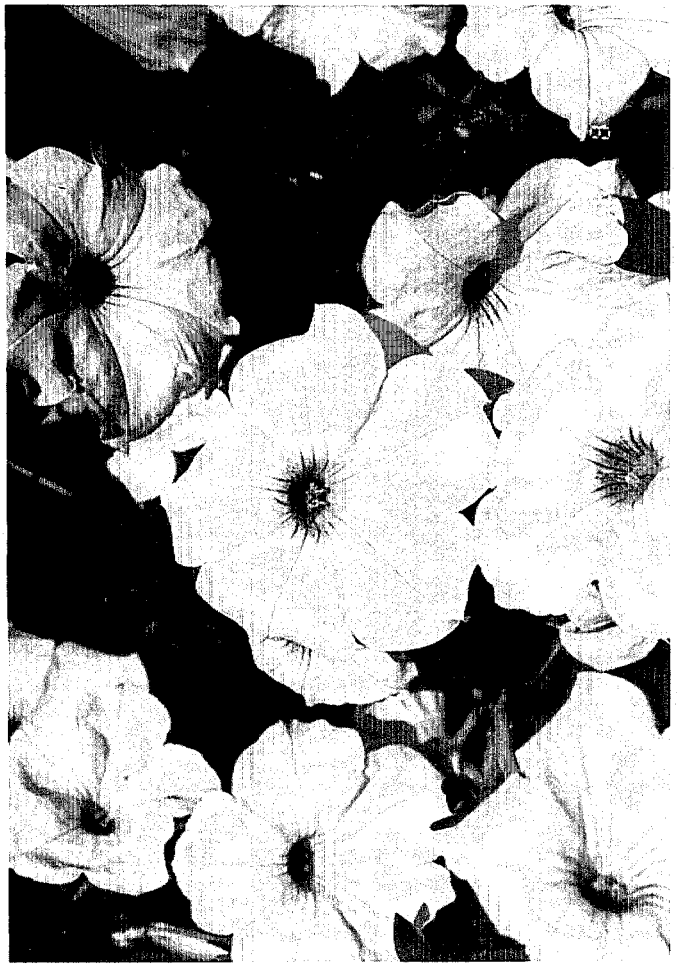
FIG. 2 is a photograph of flowers of the new variety of petunia plant.
Figure 3:
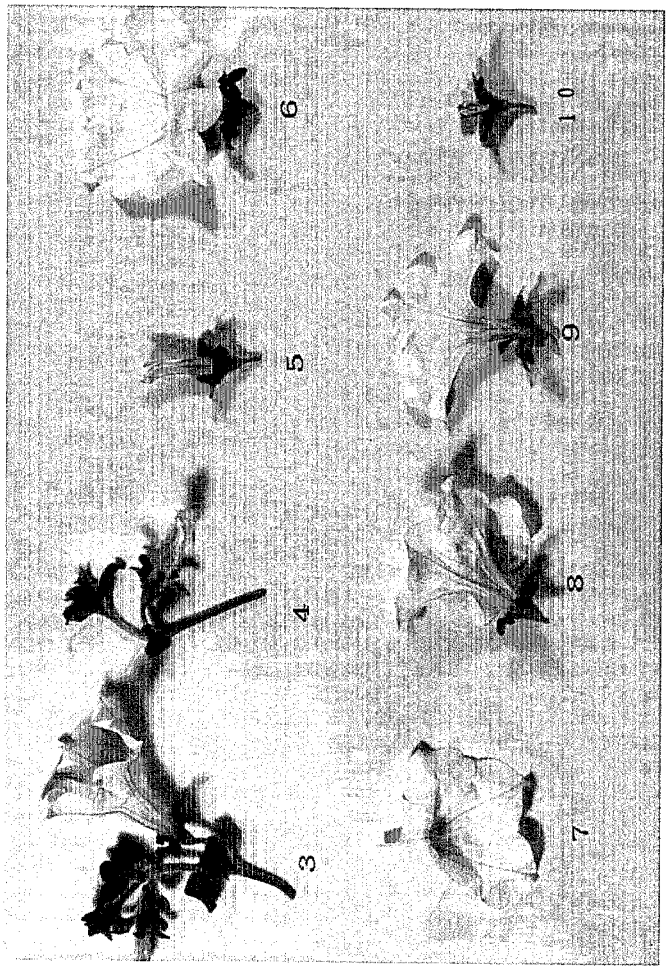
FIG. 3 is a photograph showing, in numerical order, a branch having an open flower (3), a current shoot (4), a bud (5), a side view of the flower (6), a front view of the flower (7), a rear view of the flower (8), an interior view of the flower (9), and pistil and stamens (10), of the new variety of petunia plant.
Figure 4:
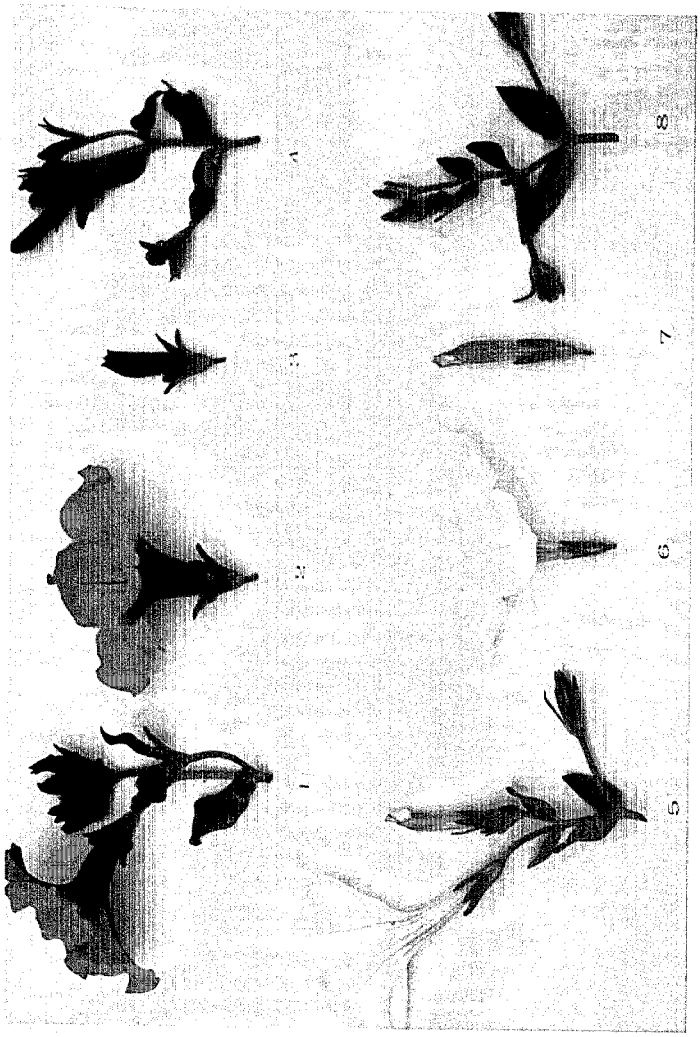
FIG. 4 is a photograph showing, in numerical order, a branch having an open flower (1), a flower (2), a bud (3), and a current shoot (4) of the comparative variety, 'Revolution Brilliantpink', in comparison with corresponding items (5–8) of the new variety.

The botanical characteristics of the new and distinct variety of petunia plant 'Revolution White' are as follows.

Plant:

*Growth habit.*—Decumbent. The stems hang down where potted in a hanging pot.

*Plant height.*—15–20 cm.

*Spreading area of plant.*—The stem extends to a length of 50–75 cm from the base, and thus the spreading area of the plant is 100–150 cm in diameter.

*Growth.*—Very vigorous with abundant branching, a great profusion of blooms; the whole bush remaining in bloom for a considerable period of time.

*Blooming period.*—Late March to late September, in the southern Kantō area, Japan. The plant shape does not change throughout this period.

Stem:

*Thickness.*—Main stem 4.0–6.5 mm.

*Anthocyanin pigmentation.*—Absent.

*Pubescence.*—Medium.

*Branching.*—Over-abundant.

*Length of internode.*—2.5–4.0 cm.

Leaf:

*Leaf attaching angle.*—Horizontal.

*Shape.*—Lanceolate.

*Size (average).*—3.5–5.5 cm×2.0–4.0 cm.

*Thickness.*—0.5 mm.

*Color.*—Strong Yellow green (R.H.S. 146A, JHS 3508).

*Pubescence.*—Medium.

Flower: Opening obliquely upward.

*Type.*—Single.

*Shape.*—Funnel-shape, with five-fissured limb.

*Shape of tip.*—Blunt.

*Lobation.*—Medium.

*Undulation of margin.*—Weak.

*Diameter.*—8.0–8.5 cm, large.

*Petal color.*—At full blooming time, yellowish white (R.H.S. 155D, JHS 2501), with vivid yellow green (R.H.S. 144B, JHS 3506) lines at petal and dull red purple (R.H.S. 70A, JHS 2903) lines at throat portion radiating from pale greenish yellow (R.H.S. 10D, JHS 2903) bottom throat portion. The outside of the petal is a yellowish white (R.H.S. 155D, JHS 2501).

*Reproductive organs.*—1 normal pistil, and 5 normal stamens. Pistil shape is thin and stamens shape is small.

*Peduncle.*—Length is medium and 1.8–2.2 mm in thickness.

Physiological and ecological characteristics: High resistance to rain, heat, drought and cold. Also high resistnace to disease, particularly gray mold (Botrytis). Moderate resistance to pest. The new variety of the present invention, just as its parent variety, has been observed to exhibit at least some self-fertility.

This new variety of petunia plant is most suitable for flower bedding and potting, particularly in hanging pots or planters, and further excellent for ground cover.

The plant of this new variety, 'Revolution White' is presently planted and maintained at the Yachiyo Farm of the Keisei Rose Nurseries, Inc., residing at 755 Ōwadasinden, Yachiyo-shi, Chiba-ken, Japan, and Plant Biotechnology Laboratory, Institute for Fundamental Research of Suntory Ltd., residing at 2913-1 Torihara, Hakushu-cho, Kitakoma-gun, Yamanashi-ken, Japan.

We claim:

1. A new and distinct variety of petunia plant, substantially as herein illustrated and described, characterized particularly as to novelty by (A) being a decumbent habit plant having long stems, (B) an abundant branching and a great profusion of blooms, the whole bush remaining in bloom for a considerable period of time, (C) flowers that are single and large, the petals having a yellowish white color with vivid yellow green lines radiating from pale greenish yellow color bottom throat portion, and (d) a high resistance to rain, heat, cold, and disease.

* * * * *